United States Patent [19]

Pitt et al.

[11] 4,379,138

[45] Apr. 5, 1983

[54] BIODEGRADABLE POLYMERS OF LACTONES

[75] Inventors: Colin G. Pitt; Anton E. Schindler, both of Durham, N.C.

[73] Assignee: Research Triangle Institute, Research Triangle Park, N.C.

[21] Appl. No.: 335,188

[22] Filed: Dec. 28, 1981

[51] Int. Cl.³ .............................................. C08G 63/08
[52] U.S. Cl. ...................... 424/78; 128/1 R; 128/92 B; 128/92 C; 528/354
[58] Field of Search ................. 528/354, 359; 424/78; 128/1 R

[56] References Cited

U.S. PATENT DOCUMENTS

| | | | |
|---|---|---|---|
| 2,362,511 | 11/1944 | Teeters | 528/361 |
| 2,758,987 | 8/1956 | Salzberg | 528/354 |
| 2,840,548 | 6/1958 | Howk et al. | 528/354 X |
| 2,890,208 | 6/1959 | Young et al. | 528/357 |
| 3,021,309 | 2/1962 | Cox et al. | 528/358 |
| 3,072,680 | 1/1963 | Starcher et al. | 528/354 X |
| 3,169,945 | 2/1965 | Hostettler et al. | 528/355 |
| 3,284,417 | 11/1966 | Hostettler et al. | 528/357 |
| 3,297,033 | 1/1967 | Schmitt et al. | 128/335.5 |
| 3,463,158 | 8/1969 | Schmitt et al. | 128/334 R |
| 3,531,361 | 9/1970 | Grandinetti | 156/582 |
| 3,620,218 | 11/1971 | Schmitt | 128/214 R |
| 3,636,956 | 1/1972 | Schneider | 128/335.5 |
| 3,736,646 | 6/1973 | Schmitt et al. | 29/458 |
| 4,045,418 | 8/1977 | Sinclair | 528/357 |
| 4,057,537 | 11/1977 | Sinclair | 528/324 |
| 4,064,086 | 12/1977 | Cowsar et al. | 528/354 X |
| 4,104,281 | 8/1978 | Onopchenko et al. | 528/354 X |
| 4,153,785 | 5/1979 | Schulz et al. | 528/354 X |
| 4,343,915 | 8/1982 | Abbey | 528/354 X |

*Primary Examiner*—Earl A. Nielsen
*Attorney, Agent, or Firm*—Cushman, Darby & Cushman

[57] ABSTRACT

Homopolymers and copolymers of lactones are prepared by ring-opening polymerization of a mixture of lactones which includes a monolactone, such as $\epsilon$-caprolactone, and a dilactone, such as bis-2,2-($\epsilon$-caprolacton-4-yl)propane, which is capable of forming crosslinks. The resulting polymers range from tough and partially crystalline to amorphous, elastomeric materials, depending on the monomer composition and proportions. Additionally, these polymers may be designed to achieve different degrees of permeability and rates of biodegradation. As such, they are useful for the controlled delivery of medicinal agents and as surgical aids and temporary artificial biomaterials such as skin substitutes and burn dressings.

13 Claims, 5 Drawing Figures

(■) C-1008, $\rho = 0.005$
(⬣) C-1009, $\rho = 0.010$
(▼) C-1010, $\rho = 0.015$
(▲) C-1011, $\rho = 0.020$
(⬢) C-1012, $\rho = 0.030$
(O) C-1014, $\rho = 0.123$

BIODEGRADABLE POLYMERS OF LACTONES

BACKGROUND OF THE INVENTION

This invention relates to novel elastomeric materials derived from polymerization of mixtures of mono- and dilactones.

Polymers are finding increasing use in the field of medicine, particularly as substitutes for the natural materials of the body. In many cases, it is desirable that the polymer be degradable, to eliminate the need for recovery or removal. Biodegradable sutures derived from polyglycolic acid and polylactic acid are examples. Biodegradable polymers are also environmentally desirable, reducing problems of waste disposal and pollution. Most of the synthetic polymers which are biodegradable are either in the glassy state or are crystalline, with the result that very few elastomeric biodegradable materials are available for use. Such is the case for polyesters.

Homopolymers and copolymers of various cyclic esters such as glycolide, lactide, δ-valerolactone, and ε-caprolactone, have been the subject of numerous patents and scientific publications, including inter-alia U.S. Pat. Nos. 2,362,511; 2,758,987; 2,890,208; 3,021,309; 3,169,945; 3,284,417; 3,297,033; 3,463,158; 3,531,361; 3,620,218; 3,636,956; 3,736,646; 4,045,418 and 4,057,537.

Polyglycolide is reported to be a hard, tough, crystalline polymer with a melting point of about 224°–226° C. and a glass transition temperature ($T_g$) of 36° C. as noted in the aforementioned U.S. Pat. No. 3,297,033. The polymer from DL-lactide is a tough, amorphous solid with a $T_g$ of about 57° C. The polymer from L-lactide is a tough partially crystalline solid, m.p. 180° C. Poly (ε-caprolactone) is described as a tough, partially crystalline solid melting at 63° C., $T_g = -60°$. Sinclair in U.S. Pat. Nos. 4,045,418 and 4,057,537 describes copolymers of ε-caprolactone and either L-lactide or DL-lactide as rigid, clear, thermoplastic solids. None of the above homopolymers and copolymers, and polymers of structurally related mono-lactones is elastomeric. However, elastomeric properties can be introduced by curing the polylactone with a peroxide such as dibenzoyl peroxide at an elevated temperature as demonstrated for example in U.S. Pat. No. 4,057,537 noted above. However, the exact structures of so-cured polymers are unknown and the property of degradation to known monomer products *in vitro* or *in vivo* is lost in this process. This reduces the biomedical value of such materials.

Accordingly, it is the primary object of the present invention to provide elastomeric lactone polymers designed to achieve different degrees of permeability, elasticity, and rates of biodegradation.

It is a further object of the present invention to provide polymers suitable for the controlled delivery of medicinal agents.

Still yet another object of our invention is to provide improved surgical aids and temporary artificial biomaterials.

These and other objects of the present invention will become more apparent from the discussion which follows.

SUMMARY OF THE INVENTION

The present invention provides for an elastomeric, biodegradable polymer formed by the ring opening polymerization of at least one monocyclic lactone and at least one polycyclic dilactone containing two lactone groups, each of which may be polymerized by ring opening to form a two-dimensional polymer.

In accordance with the present invention, biodegradable polymers are obtained by ring opening polymerization of a mixture of at least one monocyclic lactone and one polycyclic dilactone. The monocyclic lactones may be any combination of lactones which can be polymerized by ring opening, to form a one-dimensional polymer, but preferred compounds are glycolide, DL-lactide, L-lactide, δ-valerolactone, ε-caprolactone, ω-dodecalactone and their alkyl- or aryl-substituted derivatives. The polycyclic dilactone may be any structure which contains two lactone groups, each of which may be polymerized by ring-opening to form a two dimensional polymer network. An example of such a structure is:

wherein $R_1$ and $R_2$, each of which may be the same or different, is an alkyl group of 1 to 8 carbon atoms.

A large variety of bis-ε-caprolactones has been described in U.S. Pat. No. 3,072,680 (the entire contents of which are incorporated herein by reference) and may be used in the present invention.

According to a further embodiment, the present invention includes a process for the preparation of the elastomeric biodegradable polymer which comprises the steps of:

(a) mixing at least one monocyclic lactone, and at least one polycyclic dilactone containing two lactone groups, together with a polymerization catalyst;

(b) degassing the mixture obtained in step (a); and (c) heating the degassed mixture for a period of time sufficient to polymerize same.

The reaction temperature may vary widely from about 80° to about 180° C., but most suitably is in the range of from about 125° to about 150° C. Likewise, the reaction time may vary considerably, but generally is in the range of about 10 to about 50 hours.

Polymers prepared by polymerization of one or more of the above monocyclic lactones and a polycyclic dilactone are insoluble in solvents and range from partially crystalline to totally amorphous solids, which may be either in the glassy or the rubbery state. A set of desired mechanical properties (elastic modulus, tensile strength) may be achieved by educated selection of the chemical structures and proportions of the monocyclic lactones and the proportion of the polycyclic dilactone used to prepare the polymer.

The described polymers have the unexpected property of being subject to degradation *in vivo* by two mechanisms. One mechanism involves aqueous hydrolysis of the ester groups in the bulk of the polymer, ultimately leading to complete breakdown of the polymer to hydroxycarboxylic acids corresponding to the lactone monomers. This mechanism is also observed *in vitro*, for example when the polymer is immersed in water at 40° C. The second mechanism of degradation is only observed *in vivo* and involves gradual attack at and erosion of the surface of the polymer. Advantageously, the absolute and relative rates of degradation by each mechanism can be predetermined by the correct choice and proportion of the monomers used to prepare the polymer.

The following examples are offered to more fully illustrate the invention, but are not to be construed as limiting the scope thereof.

EXAMPLE ONE

A series of copolymers of $\epsilon$-caprolactone and $\delta$-valerolactone crosslinked to different degrees with 2,2-Bis($\epsilon$-caprolacton-4-yl) propane (BCP). A comonomer composition of 50 mol-percent $\delta$-valerolactone and $\epsilon$-caprolactone was charged with BCP into Teflon coated sheet or rod molds and placed in a reactor along with from 100 to 500 ppm tin octoate. The reactor was then degassed and polymerization carried out for the time and temperature conditions noted in Tables 1 and 2 below, together with the tensile properties of the resulting products.

TABLE 1

| Sample Number | Comonomers[a] (mmol) | BCP (mmol) | Temperature (°C.) | Time (hrs) | % Crosslink Density[b] |
|---|---|---|---|---|---|
| C-1001 | 49.5 | 0.154 | 140 | 64 | 0.62 |
| C-1002 | 49.5 | 0.126 | 140 | 64 | 0.91 |
| C-1003 | 57.9 | 0.180 | 140 | 40 | 0.62 |
| C-1004 | 57.9 | 0.121 | 140 | 40 | 0.42 |
| C-1007 | 28.1 | 0.308 | 140 | 36 | 2.14 |

| Sample | Rod Diameter (cm) | Young's Modulus | Nominal Stress at Break | Draw Ratio | True Stress at Break |
|---|---|---|---|---|---|
| C-1003 | 0.143 | 5.5 | 33 | 19 | 630 |
| C-1004 | 0.147 | 2.2 | 17 | 21 | 360 |
| C-1007 | 0.133 | 10.4 | 112 | 30 | 3360 |

[a]Comonomer composition: 50 mol-% $\delta$-valerolactone and $\epsilon$-caprolactone.
[b]100% conversion assumed.

Figure 1:
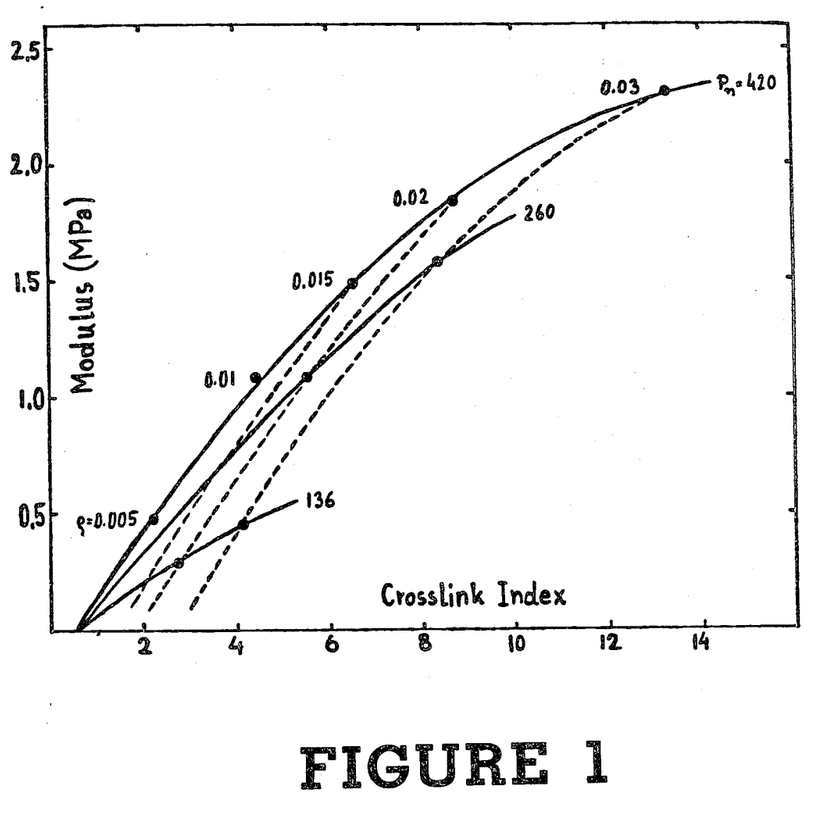
FIG. 1, is a graphic relationship between crosslink density ---, primary chain length----, and elastic modulus (1 MPa=10.2 kg/cm$^2$) of crosslinked copolymers of $\epsilon$-caprolactone and $\delta$-valerolactone.

The relationship between the crosslink density, primary chain length and elastic modulus of these crosslinked copolymers are depicted in FIG. 1.

TABLE 2

Preparation of Rods from $\delta$-Valerolactone and $\epsilon$-Caprolactone Crosslinked With 2,2-Bis($\epsilon$-caprolacton-r-yl)propane.

| Sample Number Crosslinked | Sample Number Uncrosslinked | Mol-% Valerolactone | % Crosslink Density | % Wt. Loss Pentane Extraction | Young's Modulus[a] (kg/cm$^2$) | Crosslink Index |
|---|---|---|---|---|---|---|
| C-1008 | C-315 | 0.49 | 0.53 | 4.3 | 4.9 | 2.2 |
| C-1009 | C-135 | 0.49 | 1.06 | 4.3 | 11.1 | 4.5 |
| C-1010 | C-315 | 0.49 | 1.56 | 4.1 | 15.0 | 6.6 |
| C-1011 | C-315 | 0.49 | 2.07 | 4.1 | 18.7 | 8.7 |
| C-1012 | C-315 | 0.49 | 3.17 | 3.9 | 23.5 | 13.3 |
| C-1013 | C-316 | 0.50 | 1.52 | — | — | 4.0 |
| C-1014 | C-316 | 0.50 | 2.02 | — | — | 5.3 |
| C-1015 | C-316 | 0.50 | 1.49 | 5.8 | 8.0 | 3.9 |
| C-1016 | C-316 | 0.50 | 2.00 | 6.5 | 10.4 | 5.2 |
| C-1017 | C-316 | 0.50 | 3.00 | 6.9 | 16.2 | 7.9 |
| C-1018 | C-317 | 0.48 | 1.50 | — | — | 2.0 |
| C-1019 | C-317 | 0.48 | 2.01 | — | 3.0 | 2.7 |
| C-1020 | C-317 | 0.48 | 3.02 | — | 4.6 | 4.1 |

Properties of Uncrosslinked Copolymers

| Sample Number | $[\eta]_{Tol}$ | $[\eta]$ | $M_n \cdot 10^{-3}$ | $M_w \cdot 10^{-3}$ | $M_w/M_n$ |
|---|---|---|---|---|---|
| C-315 | 0.840 | 0.905 | 45.0 | 80.1 | 1.78 |
| C-316 | 0.590 | 0.627 | 28.0 | 50.1 | 1.79 |
| C-317 | 0.309 | 0.373 | 14.6 | 25.6 | 1.76 |

[a]Rod diameters 1.4 mm except for C-1013 and C-1014, which were 6.2 mm.

EXAMPLE TWO

The degradation of selected members of the sample series of Example One in both water and 2 N acetic acid was studied in order to determine the effect of crosslink density on the rate of hydrolytic chain scission and loss of form stability, as well as to complement *in vivo* studies. (Previous studies have shown that degradation in aqueous acetic acid both reproduces and accelerates the autocatalyzed bulk hydrolysis of aliphatic polyesters). Irradiated samples were included to facilitate comparison with the *in vivo* results.

Copolymer rods, 6 cm length, were placed in screw-capped vials in about 15 ml of deionized water or 2 N acetic acid at 40° C. At given intervals, rods were removed, blotted, and weighed to determine water uptake. The rods were then dried *in vacuo* at 50° C. and reweighed to determine weight loss due to degradation. The extent of degradation was monitored by measuring the modulus. The results are summarized in Table 3 below.

TABLE 3

| Time (hrs) | % Weight Loss | | | | | Young's Modulus | | | | |
|---|---|---|---|---|---|---|---|---|---|---|
| | C-1008 | C-1009 | C-1010 | C-1011 | C-1012 | C-1008 | C-1009 | C-1010 | C-1011 | C-1012 |
| Crosslink Density | 0.53 | 1.06 | 1.56 | 2.07 | 3.17 | 0.53 | 1.06 | 1.56 | 2.07 | 3.17 |
| Degradation of Unirradiated Samples in Water | | | | | | | | | | |
| 0 | — | — | — | — | — | 4.8 | 11.0 | 15.1 | 18.8 | 23.6 |
| 280 | — | — | — | — | — | 4.2 | 10.5 | 14.4 | 17.1 | 27.7 |
| 669 | 0.2 | 0.1 | 0.6 | 0.2 | 0.3 | 3.2 | 8.8 | 12.9 | 16.2 | 21.4 |

TABLE 3-continued

| Time (hrs) | % Weight Loss | | | | | Young's Modulus | | | | |
|---|---|---|---|---|---|---|---|---|---|---|
| | C-1008 | C-1009 | C-1010 | C-1011 | C-1012 | C-1008 | C-1009 | C-1010 | C-1011 | C-1012 |
| 1000 | 0.3 | 0.1 | 0.1 | 0.2 | 0.4 | 1.1 | 6.0 | 10.0 | 13.6 | 20.0 |
| 1353 | 0.4 | 0.3 | 0.3 | 0.5 | — | 3.3 | 6.9 | 10.1 | 16.4 | |
| 1658 | — | 0.3 | 0.4 | 0.4 | 0.6 | — | 2.5 | 5.1 | 7.6 | 14.5 |
| Degradation of Irradiated (1.8 Mrad) Samples in Water | | | | | | | | | | |
| 0 | — | — | — | — | — | 3.9 | 9.3 | 13.2 | 16.8 | 21.8 |
| 383 | 0 | 0.2 | 0.2 | 0.3 | 0.3 | 2.8 | 8.0 | 12.1 | 16.2 | 20.9 |
| 712 | 0.1 | 0.2 | 0.2 | 0.4 | 0.3 | 2.3 | 6.5 | 10.4 | 14.4 | 19.8 |
| 1052 | 0 | 0.2 | 0.2 | 0.4 | 0.4 | 0.8 | 4.5 | 8.9 | 12.3 | 17.6 |
| 1534 | 0.1 | 0.3 | 0.3 | 0.5 | 0.5 | — | 3.9 | 6.2 | 9.8 | 15.1 |
| Degradation of Unirradiated Samples in Acetic Acid | | | | | | | | | | |
| 0 | — | — | — | — | — | 4.8 | 11.0 | 15.1 | 18.8 | 23.6 |
| 96 | — | 0.1 | 0.1 | 0.1 | 0.2 | 0.6 | 3.6 | 7.0 | 10.8 | 15.3 |
| 183 | — | 0.6 | 0.4 | 0.4 | 0.5 | — | 1.2 | 3.4 | 6.0 | 11.7 |
| 324 | — | 0.3 | 0.1 | 0.6 | 0.5 | — | — | 0.8 | 2.0 | 5.7 |
| 424 | — | — | 0.5 | 0.9 | 0.8 | — | — | — | 0.8 | 3.9 |
| 1113 | — | — | 5.0 | 7.7 | 7.8 | — | — | — | — | — |

The average water uptake of samples after 300 hours in water remained constant at about 1.5%, irrespective of the crosslink density of the samples. Weight losses remained negligible as long as samples preserved their geometry. Significant weight loss coincided with complete loss of shape of the rods.

Figure 2:
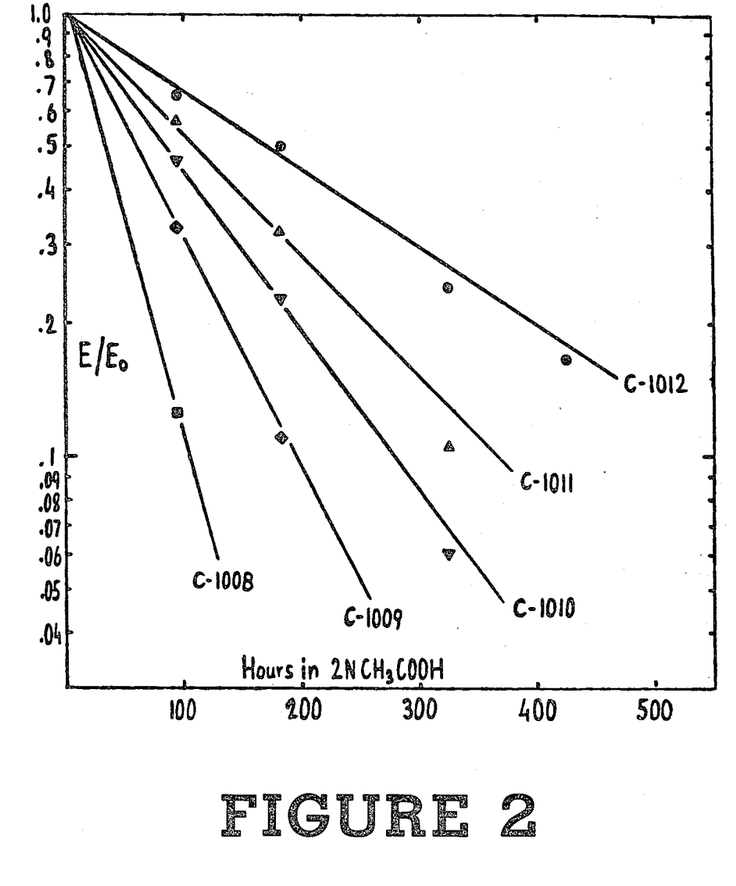
FIG. 2 is a graph showing the change in elastic modulus of $\delta$-valerolactone-co-$\epsilon$-caprolactone polymers with different crosslink densities as a function of time in 2 N acetic acid at 40° C.
Figure 3:
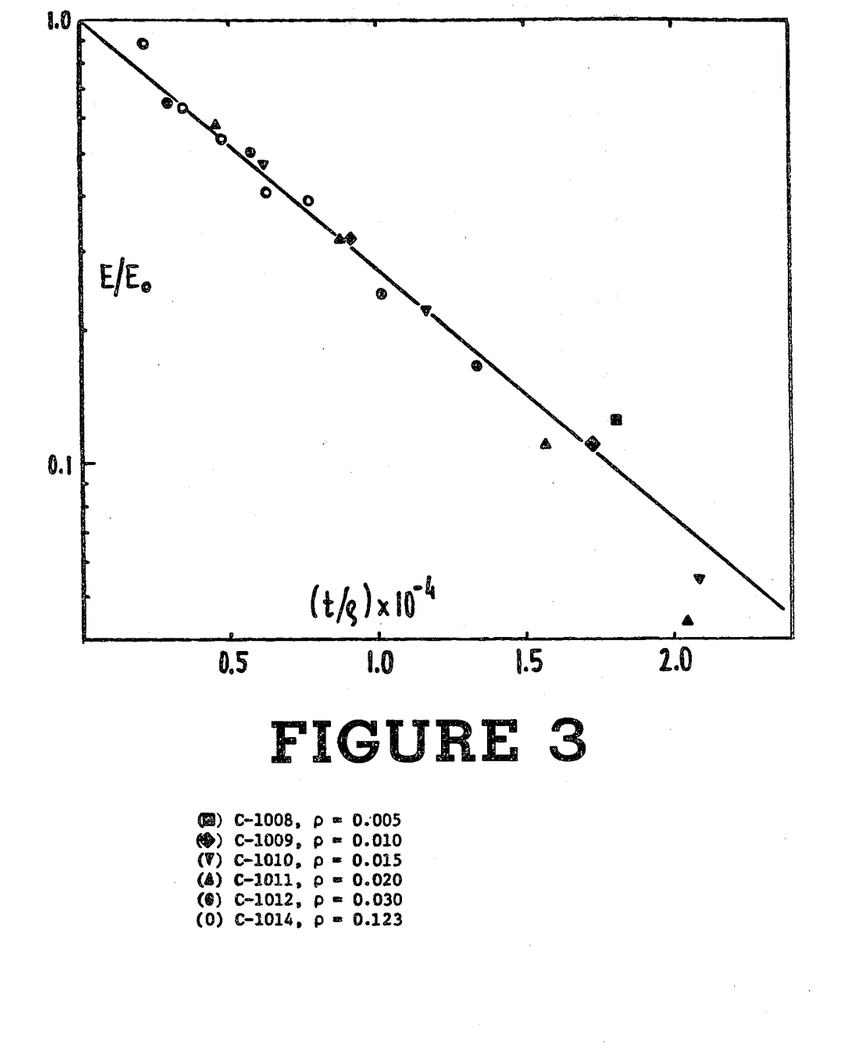
FIG. 3 is a graph showing the change in elastic modulus of $\delta$-valerolactone-co-$\epsilon$-caprolactone polymers with different crosslink densities, $\rho$, as a function of time/crosslink density in 2 N acetic acid at 40° C.

The modulus (E) of rods in 2 N acetic acid was found to decrease logarithmically with time (FIG. 2), the rate constant being inversely proportional to the crosslink density. Thus, the plot of $\ln(E/E_o)$ versus (time/$\rho$) for all of the copolymers fell on a single straight line (FIG. 3). Rate constants for the hydrolytic chain cleavage of the copolymers were derived from the modulus measurements by means of FIG. 1, where the dashed lines represent changes in modulus for constant crosslink density but changing primary chain length. During the initial phase of hydrolysis the crosslink density of the polymer can be considered constant, whereas the primary chain length decreases due to random cleavage of chain segments between crosslinks. Consequently, the decrease in the modulus should follow the dashed curves in FIG. 1. Thus, the primary chain length can be derived from each modulus measurement.

Figure 4:
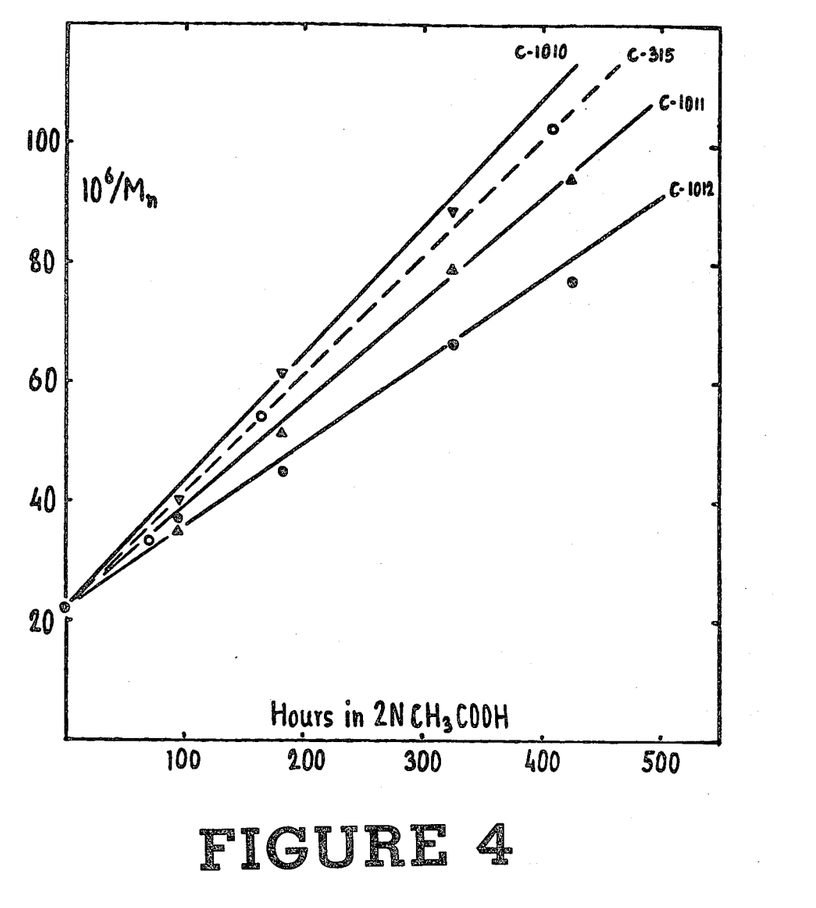
FIG. 4 is a graphic relationship between time in 2 N acetic acid at 40° C. and the molecular weight of the primary chains of crosslinked copolymers of $\delta$-valerolactone and $\epsilon$-caprolactone.

The results of this analysis of modulus measurements of rods in 2 N acetic acid are summarized graphically in FIG. 4 as a plot of the reciprocal of the molecular weight of the primary chains vs time. Linear plots are obtained, as required for acid catalyzed hydrolytic chain cleavage. The rate constants derived from the slopes of the linear plots are in good agreement with the value found for the uncrosslinked copolymers:

VL-CL (uncrosslinked)—$2.01 \times 10^{-7}$ mol.g.$^{-1}$h.$^{-1}$
C-1010—$2.07 \times 10^{-7}$
C-1011—$1.75 \times 10^{-7}$
C-1012—$1.30 \times 10^{-7}$ Changes in the modulus of unirradiated and $\gamma$-irradiated (1.8 Mrad) copolymers of $\delta$-valerolctone and $\epsilon$-caprolactone, crosslinked with BCP, are summarized in Table 3. No significant weight loss was detected in 69 days.

EXAMPLE THREE

In order to establish the relationship between crosslink density and the biodegradation rate, rods (6 cm length × 1.4 mm diameter) of the copolymers were sterilized by—irradiation and implanted in the dorsal region of 7 New Zealand white rabbits following the standard protocol. Five copolymers with different crosslink densities (0.5, 1.0, 1.5, 2.0, and 3.0%) were implanted in each rabbin, together with a sealed but empty poly($\epsilon$-caprolactone) capsule (2 cm length) as control. Single animals were sacrificed after 2, 5, 7, 10, 12, and 16 weeks, and the implants were recovered.

All of the excised copolymer rods, even those removed after only 2 weeks, were substantially encapsulated by tissue; in contrast, the poly($\epsilon$-caprolactone) controls were free of adhering tissue. In order to obtain accurate weight loss and modulus data, this tissue was removed by immersing the rods in a 1% trypsin solution, pH 7.2, overnight. Weight loss and modulus measurements are listed in Table 4 below, while Table 5 shows the changes in primary chain length calculated from the modulus data.

Figure 5:
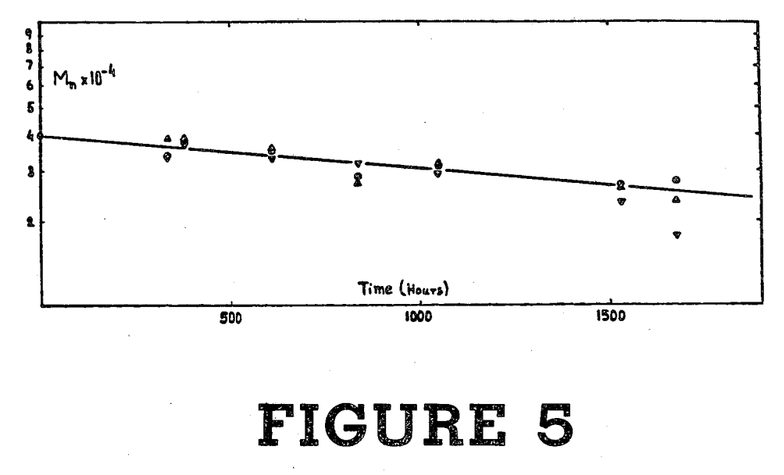
FIG. 5 shows the molecular weight change of primary chains in $\gamma$-irradiated (1.8 Mrad) crosslinked rods of poly ($\delta$-valerolactone-co-$\epsilon$caprolactone) during degradation in rabbits (full signs) and in water at 40° C. (open signs).

Considering first the primary chain length data, which reflect the rate of hydrolytic cleavage of chain segments between crosslinks, the data in the last two columns in Table 5 compare the primary chain lengths after 2, 5, and 10 weeks *in vivo* and *in vitro*. A close correspondence between the two sets of data is evident and, indeed, the graphical presentation in FIG. 5 shows that the degradation rates *in vivo* and *in vitro* are identical within experimental error.

In contrast to this parallel behavior, there was a marked difference in the rates of weight loss *in vivo* and *in vitro*. Under *in vivo* conditions there was significant weight loss from all of the copolymers, even after only 2 weeks, which increased to 50% after 10 weeks and 100% after 16 weeks. No weight loss was observed under *in vitro* ($H_2O$, 40° C.) conditions during the same time period.

The modulus and weight loss data suggest that these crosslinked copolymers are being degraded *in vivo* by a different mechanism than has been observed previously with other aliphatic polyesters. This is the first time that continuous weight loss of polyesters has been observed *in vivo*, with a different *in vivo* and *in vitro* behavior. It seems that the crosslinked copolymers are degraded by two mechanisms. One is the same mechanism which occurs under *in vitro* conditions, namely hydrolytic chain cleavage randomly throughout the bulk of the sample. The second mechanism is restricted to attack at the sample surface. The bulk process occurs at the same rate under both *in vitro* and *in vivo* conditions; the surface erosion process proceeds at a considerably higher rate than the bulk process. The absence of surface erosion *in vitro* suggests that it may be enzymatic.

TABLE 4

In Vivo Degradation of Crosslinked Copolymers of δ-Valerolactone and ε-Caprolactone in Rabbit.

| Time (Weeks) | % Weight Loss | | | | | Young's Modulus | | | | |
|---|---|---|---|---|---|---|---|---|---|---|
| | C-1008 | C-1009 | C-1010 | C-1011 | C-1012 | C-1008 | C-1009 | C-1010 | C-1011 | C-1012 |
| 0 | — | — | — | — | — | 3.9 | 9.3 | 13.2 | 16.8 | 21.8 |
| 2 | 46.1 | 12.2 | 15.1 | 6.2 | 13.5 | a | 7.1 | 10.5 | 16.2 | 19.1 |
| 5 | 72.2 | 59.0 | 61.6 | 69.6 | 63.5 | b | b | 9.8 | 10.4 | 16.2 |
| 7 | 35.9 | 47.6 | 83.4 | 62.5 | 79.5 | c | a | b | a | a |
| 10 | 39.0 | 50.4 | 69.3 | 62.6 | 52.8 | c | a | 3.8 | 8.4 | 15.6 |
| 12 | d | 99.2 | 84.7 | 99.0 | 97.5 | — | — | — | — | — |
| 16 | d | e | e | 99.3 | 93.4 | — | — | — | — | — |

[a]Rod of very uneven cross section
[b]Rod broken into pieces
[c]no form stability
[d]sticky smear, could not be weighed
[e]no sample found

TABLE 5

Evaluation of Modulus Data of Crosslinked Copolymers of δ-Valerolactone and ε-Caprolactone After Degradation In Vivo.

| Time (weeks) | Polymer Designation | Modulus (MPa) | Crosslink Index | Primary Chain Length | | |
|---|---|---|---|---|---|---|
| | | | | Individual | Average | From FIG. 5 |
| 2 | C-1010 | 1.03 | 4.85 | 311 | | |
| | C-1011 | 1.59 | 7.60 | 367 | 331 ± 32 | 351 |
| | C-1012 | 1.87 | 9.95 | 314 | | |
| 5 | C-1010 | 0.96 | 4.60 | 295 | | |
| | C-1011 | 1.02 | 5.30 | 256 | 273 ± 20 | 300 |
| | C-1012 | 1.59 | 8.45 | 267 | | |
| 10 | C-1010 | 0.37 | 2.55 | 163 | | |
| | C-1011 | 0.82 | 4.55 | 220 | 213 ± 47 | 238 |
| | C-1012 | 1.53 | 8.15 | 257 | | |

Control of Degradation

The rate of bioabsorption may be controlled by variation of the crosslink density of the polymer, as illustrated by the Example 4. Alternatively, the rate of bioabsorption may be controlled by an educated change in the chemical composition of the monomers, as is demonstrated in Example 5.

EXAMPLE 4

Compolymers containing an equimolar ratio of δ-valerolactone and ε-caprolactone were prepared using amounts of BCP calculated to achieve 6.1% and 11.2% crosslink densities. Rods of each composition were implanted in rabbit, and sample recovered after 4, 9, and 17 weeks. Weight losses and changes in Young's moduli of the recovered samples are listed in Table 6. The data in this Table and in Table 3 establish that the rate of bioabsorption is inversely proportional to the crosslink density.

EXAMPLE 5

Three copolymers of ε-caprolactone, 4-t-butyl-caprolactone, and BCP, with the same crosslink density of 3.6% but with increasing amounts of 4-t-butyl-ε-caprolactone were prepared and rods were implanted in rabbit. Samples were recovered after 4, 9, 14 and 20 weeks, and weight loss and Young's moduli were measured. The results are shown in Table 7 and establish that the rate of weight loss is dependent on the 4-t-butyl-ε-caprolactone content.

The elasticity may be controlled by choice of the appropriate crosslink index, as is evident from the data presented in FIG. 1.

TABLE 6

In Vivo Degradation of Crosslinked Copolymers of δ-Valerolactone and ε-Caprolactone in Rabbit.[a]

| Polymer No. | % Weight Loss | | Young's Modulus (kg/cm²) | |
|---|---|---|---|---|
| % Crosslink Density Time (Weeks) | C-1032 6.1% | C-1033 11.2% | C-1032 6.1% | C-1033 11.2% |
| 0 | — | — | 30.0 | 37.0 |
| 4 | 9.7 | 1.8 | 32.2 | 37.0 |
| 9 | 17.4 | — | 24.8 | — |
| 17 | 33.4 | 7.0 | 19.4 | 24.8 |

[a]Comonomer ratio 1:1.

TABLE 7

In Vivo Degradation of Crosslinked Copolymers of 4-5-Butyl-ε-caprolactone (TBCL) and ε-Caprolactone in Rabbit.[a]

| Polymer No. | | % Weight Loss | | | Young's Modulus (kg/cm²) | | |
|---|---|---|---|---|---|---|---|
| Mol-% TBCL Time (Weeks) | Rabbit Number | C-1029 14.0% | C-1030 29.5% | C-1031 46.3% | C-1029 14.0% | C-1030 29.5% | C-1031 46.3% |
| 0 | — | — | — | — | 23.3 | 16.4 | 11.7 |
| 4 | 140 | 4.7 | 1.5 | 0.9 | 17.9 | 13.6 | 9.2 |
| 9 | 141 | 29.6 | 9.1 | 5.5 | 11.4 | 8.9 | 6.3 |
| 14 | 142 | 27.2 | 7.9 | 3.5 | 9.5 | 7.8 | 4.2 |
| 20 | 140 | 44.6 | 15.3 | 7.7 | 4.5 | 3.6 | 2.3 |

[a]Crosslink density 3.6%.

We claim:

1. An elastomeric, biodegradable polymer formed by the opening polymerization of at least one monocyclic lactone and at least one polycyclic dilactone containing two lactone groups, each of which may be polymerized by ring opening to form a two-dimensional polymer.

2. The polymer of claim 1 wherein said monocyclic lactone is selected from the group consisting of glycolide, DL-lactide, L-lactide, δ-valerolactone, ε-caprolactone, ω-dodecalactone and the $C_{1-8}$ alkyl and aryl derivatives thereof.

3. The polymer of claim 1 or 2 wherein said dilactone is of the formula:

wherein $R_1$ and $R_2$, each of which may be the same or different, is an alkyl group of 1 to 8 carbon atoms.

4. The polymer of claim 3 wherein said dilactone is 2,2-bis(ε-caprolacton-4-yl)propane.

5. The polymer of claim 4 wherein the monocyclic lactone is a mixture of δ-valerolactone and ε-caprolactone.

6. The polymer of claim 1 containing from about 0.5 to about 20 mole percent of said dilactone.

7. The polymer of claim 6 wherein said dilactone is present in an amount ranging from about 3 to about 10 mole percent.

8. A process for the preparation of the elastomeric biodegradable polymer of claim 1 which comprises the steps of:
 (a) mixing at least one monocyclic lactone, and at least one polycyclic dilactone containing two lactone groups, together with a polymerization catalyst;
 (b) degassing the mixture obtained in step (a); and
 (c) heating the degassed mixture for a period of time sufficient to polymerize same.

9. A process according to claim 8 wherein said degassed mixture is heated at a temperature ranging from about 80° to about 180° C.

10. A process according to claim 9 wherein the degassed mixture is heated from about 125° to 150° C.

11. A process according to claim 9 wherein said degassed mixture is heated for a period of from 10 to about 50 hours.

12. A pharmaceutical preparation comprising a pharmaceutically acceptable medicinal agent as an active ingredient dissolved or dispersed in the biodegradable polymer of claim 1.

13. A prosthesis formed from the polymer of claim 1.